(12) United States Patent
Gamache

(10) Patent No.: US 9,377,444 B2
(45) Date of Patent: Jun. 28, 2016

(54) DIAPHRAGM-SEALED VALVE WITH IMPROVED ACTUATOR DESIGN

(71) Applicant: Mécanique Analytique Inc., Thetford-Mines (CA)

(72) Inventor: Yves Gamache, Adstock (CA)

(73) Assignee: Mécanique Analytique Inc., Thetford-Mines (CA)

( * ) Notice: Subject to any disclaimer, the term of this patent is extended or adjusted under 35 U.S.C. 154(b) by 54 days.

(21) Appl. No.: 14/377,670

(22) PCT Filed: Feb. 18, 2013

(86) PCT No.: PCT/CA2013/050124
§ 371 (c)(1),
(2) Date: Aug. 8, 2014

(87) PCT Pub. No.: WO2013/120208
PCT Pub. Date: Aug. 22, 2013

(65) Prior Publication Data
US 2015/0083259 A1 Mar. 26, 2015

Related U.S. Application Data

(60) Provisional application No. 61/599,553, filed on Feb. 16, 2012.

(51) Int. Cl.
*F16K 11/078* (2006.01)
*G01N 30/20* (2006.01)
(Continued)

(52) U.S. Cl.
CPC ............... *G01N 30/20* (2013.01); *F16K 11/02* (2013.01); *F16K 11/20* (2013.01); *F16K 31/1225* (2013.01); *G01N 2030/205* (2013.01); *G01N 2030/328* (2013.01); *Y10T 137/87716* (2015.04)

(58) Field of Classification Search
CPC ..... F16K 11/20; F16K 11/02; F16K 31/1225; G01N 2030/328; G01N 2030/205; G01N 30/20; Y10T 137/87716
USPC ........................... 137/625.17, 625.28, 625.49
See application file for complete search history.

(56) References Cited

U.S. PATENT DOCUMENTS 3,203,249 A 8/1965 Jentzsch et al.
3,297,053 A 1/1967 McKinney
(Continued)

FOREIGN PATENT DOCUMENTS

WO 2009/073966 A1 6/2009
WO 2010111791 10/2010

OTHER PUBLICATIONS

International Search Report, Canadian Intellectual Property Office, Apr. 18, 2013.

*Primary Examiner* — John K Fristoe, Jr.
*Assistant Examiner* — Umashankar Venkatesan
(74) *Attorney, Agent, or Firm* — Price Heneveld LLP

(57) ABSTRACT

A valve includes a valve cap, a valve body and a diaphragm positioned between the valve cap and the valve body. The valve further includes a plurality of plungers movable, by an actuation system, between a closed position where the plunger engages the diaphragm, and an open position where the plunger is disengaged from the diaphragm. Each plunger includes a base section connected to the actuation system and a head projecting away therefrom, a top section extending between the base section and the diaphragm, wherein the top section includes a foot in contact with the head of the base section, and a biasing mechanism biasing the top section away from the diaphragm when the plunger is in the open position. Tangential contact points may also be provided between components of the actuation and the biasing mechanism for preventing a misalignment of the actuation system within the valve body.

18 Claims, 13 Drawing Sheets

(51) Int. Cl.
  *F16K 11/20* (2006.01)
  *F16K 11/02* (2006.01)
  *F16K 31/122* (2006.01)
  *G01N 30/32* (2006.01)

(56) References Cited

U.S. PATENT DOCUMENTS

| | | |
|---|---|---|
| 4,550,742 A | 11/1985 | Stearns |
| 4,795,130 A | 1/1989 | Price et al. |
| 5,601,115 A * | 2/1997 | Broerman ............ F16K 11/0743 137/595 |
| 6,202,698 B1 * | 3/2001 | Stearns .................... F16K 11/22 137/595 |
| 7,216,528 B2 | 5/2007 | Gamache et al. |
| 2009/0152481 A1 * | 6/2009 | Gamache ................ F16K 11/20 251/12 |
| 2010/0059699 A1 * | 3/2010 | Gamache .................. F16K 7/16 251/213 |

* cited by examiner

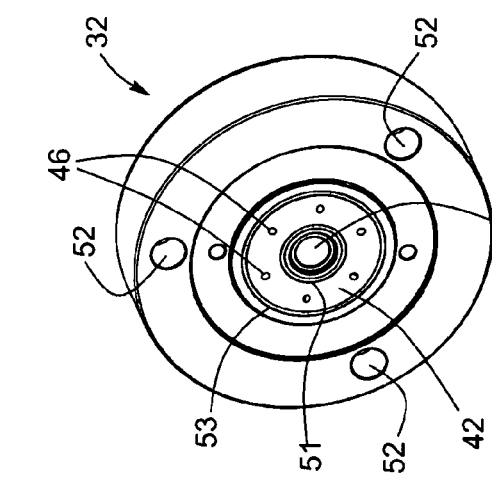

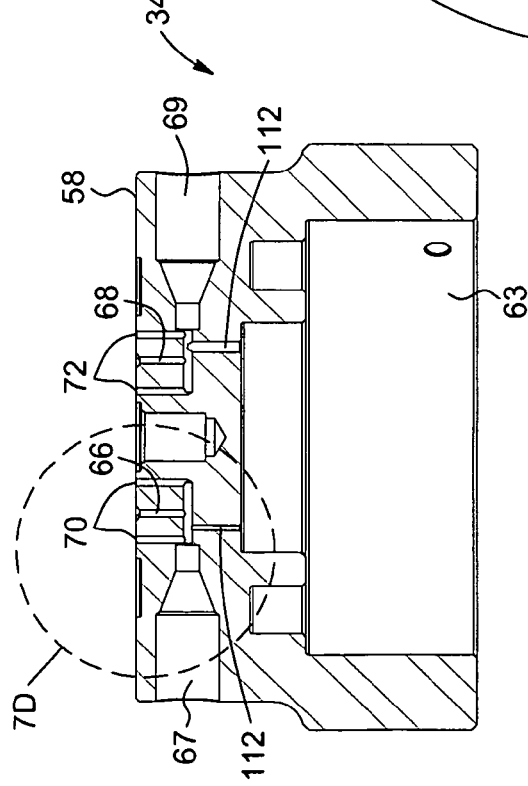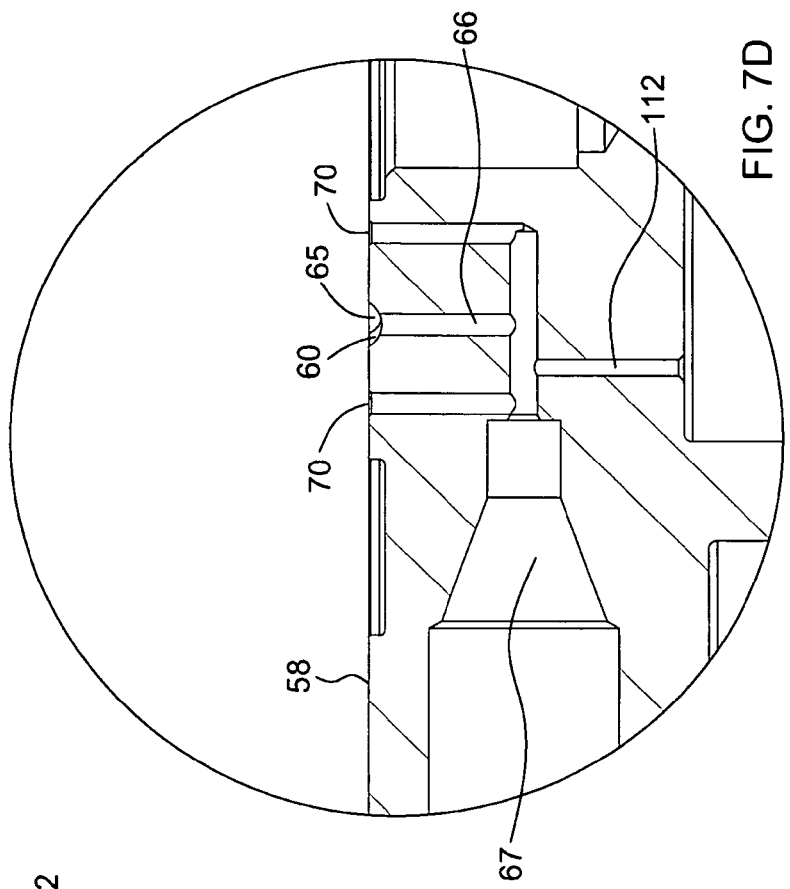

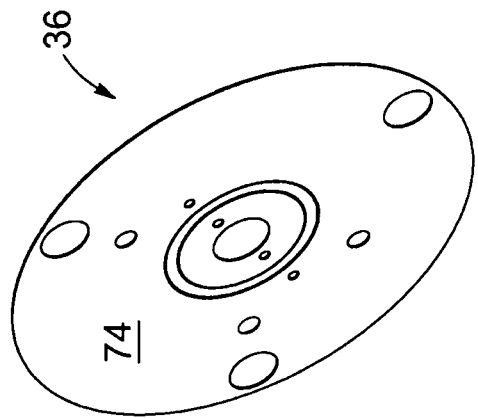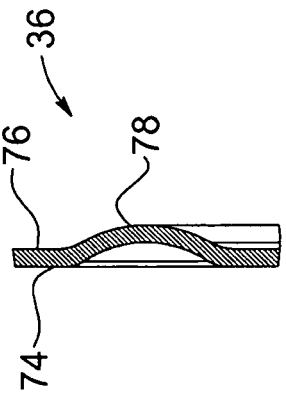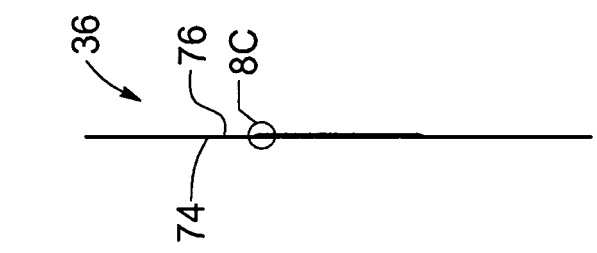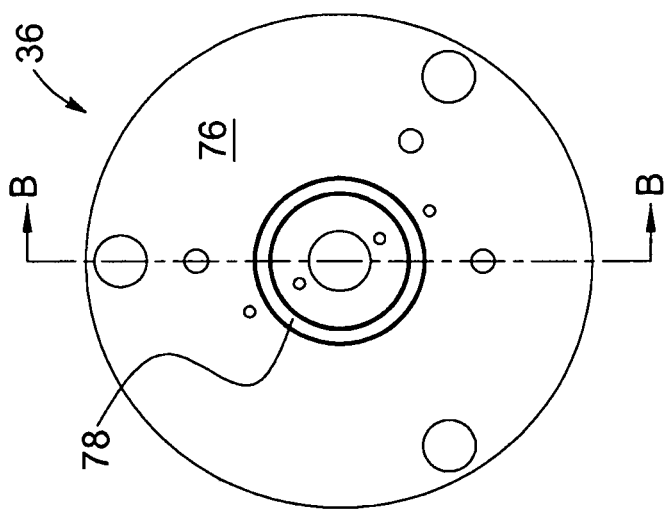

DIAPHRAGM-SEALED VALVE WITH IMPROVED ACTUATOR DESIGN

FIELD OF THE INVENTION

The present invention generally relates to fluid analytical systems and more particularly concerns a diaphragm-sealed valve having improved plungers, actuation system and/or biasing mechanism and a valve assembly comprising the same.

BACKGROUND OF THE INVENTION

As well known by those skilled in the art, chromatographic systems rely on the use of valves to allow reproducible sample introduction and various column switching schemes.

Diaphragm valves of various designs are known in the art for chromatography applications. Such diaphragm valves have been used in many commercially available gas chromatographs. They are apt to be integrated more easily in a gas chromatograph due to their physical size and since the actuator is embedded in the valve itself. These characteristics make them attractive for gas chromatograph manufacturers.

For example, international application No. PCT/CA2008/002138, filed Dec. 5, 2008 by the present applicant and published as WO2009/073966, as well as international application no. PCT/CA2009/001783, also by the present applicant, and published as WO2010/063125, disclose such a diaphragm-sealed valve. In addition, U.S. Pat. Nos. 7,216,528 and 7,503,203 issued to the present applicants on May 15, 2007 and Mar. 17, 2009, respectively, disclose other variants of diaphragm-sealed valves.

Referring to FIG. 1 (PRIOR ART), there is shown an example of a typical diaphragm-sealed valve as known in the art. The valve 1 is provided with a top block 2 having an interface 4 and a plurality of ports 6. Each one of the ports 6 opens at the interface 4 and has a thread passage 8 to connect various analytical fitting and tubing (not shown). At the bottom of the thread passage 8, there is a conduit 10 extending in the top block 2 and opening into ports 6 at the interface 4. The ports 6 are arranged along a line, such as, for example, a circular line, on the interface 4 of the top block 2. The interface 4 is advantageously flat and polished to minimize leaks between ports 6 and from the ambient atmosphere. The valve 1 is also provided with a bottom block 12 and a diaphragm 14, which is generally made of material such as polyimide, Teflon™ (polytetrafluoroethylene) or other polymers. The diaphragm 14 is positioned between the top block interface 4 and the bottom block 12, and has a recess 18 therein extending along a line formed by the ports 6 and biased away from the interface 4 of the top block 2. The recess 18 in the diaphragm 14 sits in a matching recess 20 made in the bottom block 12, thereby allowing some clearance for fluid circulation between adjacent ports 6.

The valve 1 is also provided with a plurality of plungers 16 mounted in the bottom block 12, each being respectively arranged to be able to compress the diaphragm 14 against the top block 2 at a position located between two of the ports 6. Preferably and as illustrated, in the case of a 6 port valve, when the valve is at rest, three plungers 16 are up while the other three are down. When the plungers are up, they compress the diaphragm 14 against the top block 2 and close the conduits made by the diaphragm recess 18, so that fluid circulation is blocked. The bottom block 12 keeps the plungers 16 and the actuation system in position.

It is common to designate a portion of the plungers 16 as "normally open" and another portion as "normally closed". A normally open plunger 16 is biased downwards, i.e. away from the diaphragm 14, and therefore normally allows fluid circulation between the two adjacent ports 6. A normally closed plunger 16 is biased upwards, i.e. towards the diaphragm 14, and therefore blocks fluid circulation between the two adjacent ports 6. A user may actuate the valve 1 in order to alter the positions of the plungers 16, for example by sliding upwards and downwards the normally open and closed plungers 16, respectively.

It has been found that for the valve to be effective in a number of applications, the components of the actuation system of the valve must be machined with a high level of mechanical tolerance and special procedures are required during assembly and testing. For example, plungers must be sorted by their length, to make sure that inside any valve, plungers have the exact same length. Moreover, extra care must be shown to ensure that plungers are aligned and centered in the plunger passages of the cylinder body and remain centered over time. Indeed, friction will eventually generate wear and resulting particles that will build up and affect valve performances, therefore, special dowel pins and precise alignment marks are often necessary. The precise assembly of the component requires skilled assembly technicians and makes the assembly process long and costly.

In view of the above, there is a need for an improved valve which, by virtue of its design and components, would be able to overcome or at least minimize some of the above-discussed prior art concerns.

SUMMARY OF THE INVENTION

According to a first general aspect, there is provided a valve which comprises a valve cap having a plurality of process conduits extending therethrough, each one of the plurality of process conduits ending in a process port at a valve cap interface. The valve also has a valve body having a valve body interface facing the valve cap interface, the valve body having a plurality of plunger passages extending therein. The valve also has a diaphragm positioned between the valve cap interface and the valve body interface, across the process ports and a plurality of plungers. Each one of the plurality of plungers is positioned in a corresponding plunger passage of the plurality of plunger passages and is movable between a closed position where the plunger engages the diaphragm, and an open position where the plunger is disengaged from the diaphragm. The valve further has an actuation system for moving each one of the plurality of plungers between the closed position and the open position. Each one of the plurality of plungers has a base section connected to the actuation system and a head projecting away therefrom; a top section extending between the base section and the diaphragm, the top section having a foot in contact with the head of the base section; and a plunger biasing mechanism biasing the top section away from the diaphragm when the plunger is in the open position.

According to another general aspect, there is provided a valve assembly for a valve having a valve cap with a plurality of process conduits extending therethrough, each one of the plurality of process conduits ending in a process port at a valve cap interface, and a diaphragm positioned across the process ports. The valve assembly comprises a valve body having a valve body interface facing the valve cap interface. The valve body has a plurality of plunger passages extending therein. The valve assembly also includes a plurality of plungers. Each one of the plurality of plungers is positioned in a corresponding plunger passage of the plurality of plunger passages and is movable between a closed position where the plunger engages the diaphragm, and an open position where the plunger is disengaged from the diaphragm. The valve assembly also includes an actuation system for moving each one of the plurality of plungers between the closed position and the open position. Each one of the plurality of plungers has a base section connected to the actuation system and a head projecting away therefrom; a top section extending between the base section and the diaphragm, the top section having a foot in contact with the head of the base section; and a biasing mechanism biasing the top section away from the diaphragm when the plunger is in the open position.

In an embodiment, the foot of the top section is in tangential contact with the head of the base section.

In an embodiment, at least one of the head of the base section or the foot of the top section presents a rounded configuration and the other one presents either a flat or a rounded configuration.

In an embodiment, the head of the base section presents a flat configuration and the foot of the top section presents a rounded configuration.

In an embodiment, each one of the plurality of plunger passages of the valve body comprises a shoulder defining a narrower portion of the passage between the shoulder and the valve body interface. The top section of each one of the plurality of plungers is sized and shaped such that a diaphragm-engaging portion of the top section is narrower than the foot and is movable in the narrower portion of the passage.

In an embodiment, the plunger biasing mechanism of each one of the plurality of plungers is located between the shoulder of a corresponding one of the plurality of plunger passages and the foot of the top section of the plunger.

In an embodiment, the plunger biasing mechanism is a spring.

In an embodiment, the actuation system comprises a piston.

In an embodiment, the actuation system further has a push plate with a horizontally centered bearing receiving section formed therein and a bearing located within the bearing receiving section of the push plate and projecting therefrom. A projecting portion of the bearing is in tangential contact with the piston and is the single point of contact between the piston and the push plate. At least one of the plurality of plungers is mounted on the push plate.

In an embodiment, the actuation system further comprises a piston biasing mechanism for biasing the piston of the actuation system upwardly. The piston biasing mechanism has a support having a horizontally centered bearing receiving section formed therein; a piston biasing element positioned between a section of the support and the piston; a bottom cap screw for adjustably pressuring the support towards the piston; and a bearing located within the bearing receiving section of the support and projecting therefrom. A projecting portion of the bearing is in tangential contact with the bottom cap screw and is the single point of contact between the support and the bottom cap screw.

In an embodiment, the support is a Belleville washer support and the piston biasing element is a Belleville washer assembly.

According to another general aspect, there is provided a valve with a valve cap having a plurality of process conduits extending therethrough, each one of the process conduits ending in a process port at a valve cap interface. The valve also has a valve body having a valve body interface facing the valve cap interface, the valve body having a plurality of plunger passages extending therein. The valve also has a diaphragm positioned between the valve cap interface and the valve body interface, across the process ports and a plurality of plungers. Each one of the plurality of plungers is positioned in a corresponding plunger passage of the plurality of plunger passages and is movable between a closed position where the plunger engages the diaphragm, and an open position where the plunger is disengaged from the diaphragm. The valve also has an actuation system for moving each one of the plurality of plungers between the closed position and the open position. The actuation system has a first actuation component having a horizontally centered bearing receiving section formed therein and a first bearing located within the bearing receiving section of the first actuation component and projecting therefrom. A projecting portion of the first bearing is in tangential contact with a second actuation component of the actuation system and is the single point of contact between the first actuation component and the second actuation component. The valve also has a biasing mechanism for biasing the second actuation component of the actuation system upwardly. The biasing mechanism has a first biasing component having a horizontally centered bearing receiving section formed therein; a biasing element positioned between a section of the first biasing component and the second actuation component; and a second bearing located within the bearing receiving section of the first biasing component and projecting therefrom. A projecting portion of the second bearing is in tangential contact with a second biasing component of the biasing system and is the single point of contact between the first biasing component and the second biasing component.

In an embodiment, the first actuation component is a push plate, the second actuation component is a piston, the first biasing component is a support and the second biasing component is a bottom cap screw.

In an embodiment, the support is a Belleville washer support and the biasing element is a Belleville washer assembly.

According to another general aspect, there is provided a valve with a valve cap having a plurality of process conduits extending therethrough, each one of the process conduits ending in a process port at a valve cap interface. The valve also has a valve body having a valve body interface facing the valve cap interface, the valve body having a plurality of plunger passages extending therein. The valve also has a diaphragm positioned between the valve cap interface and the valve body interface, across the process ports and a plurality of plungers. Each one of the plurality of plungers is positioned in a corresponding plunger passage of the plurality of plunger passages and is movable between a closed position where the plunger engages the diaphragm, and an open position where the plunger is disengaged from the diaphragm. The valve also has an actuation system for moving each one of the plurality of plungers between the closed position and the open position. The actuation system has a piston; a push plate having a horizontally centered bearing receiving section formed therein, at least one of the plurality of plungers being mounted on the push plate; and a bearing located within the bearing receiving section of the push plate and projecting therefrom. A projecting portion of the bearing is in tangential contact with the piston and is the single point of contact between the piston and the push plate.

According to another general aspect, there is provided a valve with a valve cap having a plurality of process conduits extending therethrough, each one of the process conduits ending in a process port at a valve cap interface. The valve also has a valve body having a valve body interface facing the valve cap, the valve body having a plurality of plunger passages extending therein. The valve also has a diaphragm positioned between the valve cap interface and the valve body interface, across the process ports and a plurality of plungers. Each one of the plurality of plungers is positioned in a corresponding plunger passage of the plurality of plunger passages and is movable between a closed position where the plunger engages the diaphragm, and an open position where the plunger is disengaged from the diaphragm. The valve also has an actuation system with a piston for moving each one of the plurality of plungers between the closed position and the open position. The valve also has a biasing mechanism for biasing the piston of the actuation system upwardly. The biasing mechanism has a support having a horizontally centered bearing receiving section formed therein; a piston biasing element positioned between a section of the support and the piston; a bottom cap screw for adjustably pressuring the support towards the piston; and a bearing located within the bearing receiving section of the support and projecting therefrom. A projecting portion of the bearing is in tangential contact with the bottom cap screw and is the single point of contact between the support and the bottom cap screw.

Advantageously, the above described valve offers similar performance as known valves while requiring less mechanical tolerances, no or minor tuning, a lower assembly time and less testing time which have a positive impact on production cost and speed.

BRIEF DESCRIPTION OF THE DRAWINGS

Other objects, advantages and features will become more apparent upon reading the following non-restrictive description of preferred embodiments thereof, given for the purpose of exemplification only, with reference to the accompanying drawings in which:

FIG. 6A is a top view of a valve cap according to an embodiment.

FIG. 6B is a cross-sectional side view of the valve cap of FIG. 6A taken along line B-B.

FIG. 6C is a cross-sectional view of the valve cap of FIG. 6A taken along the line C-C.

FIGS. 6D and 6E are a bottom perspective view and a top perspective view of the valve cap of FIG. 6A, respectively.

FIG. 7C is a cross-sectional side view of the cylinder of FIG. 7A taken along line C-C.

FIG. 7D is an enlarged view of section 7D of FIG. 7C.

FIG. 8A is a bottom view of a diaphragm according to an embodiment.

FIG. 8B is a cross-sectional side view of the diaphragm of FIG. 8A taken along line B-B.

FIG. 8C is an enlarged view of section 8C of FIG. 8B.

FIG. 8D is a top perspective view of the diaphragm of FIG. 8A.

DETAILED DESCRIPTION OF THE PREFERRED EMBODIMENTS

Figure 1:
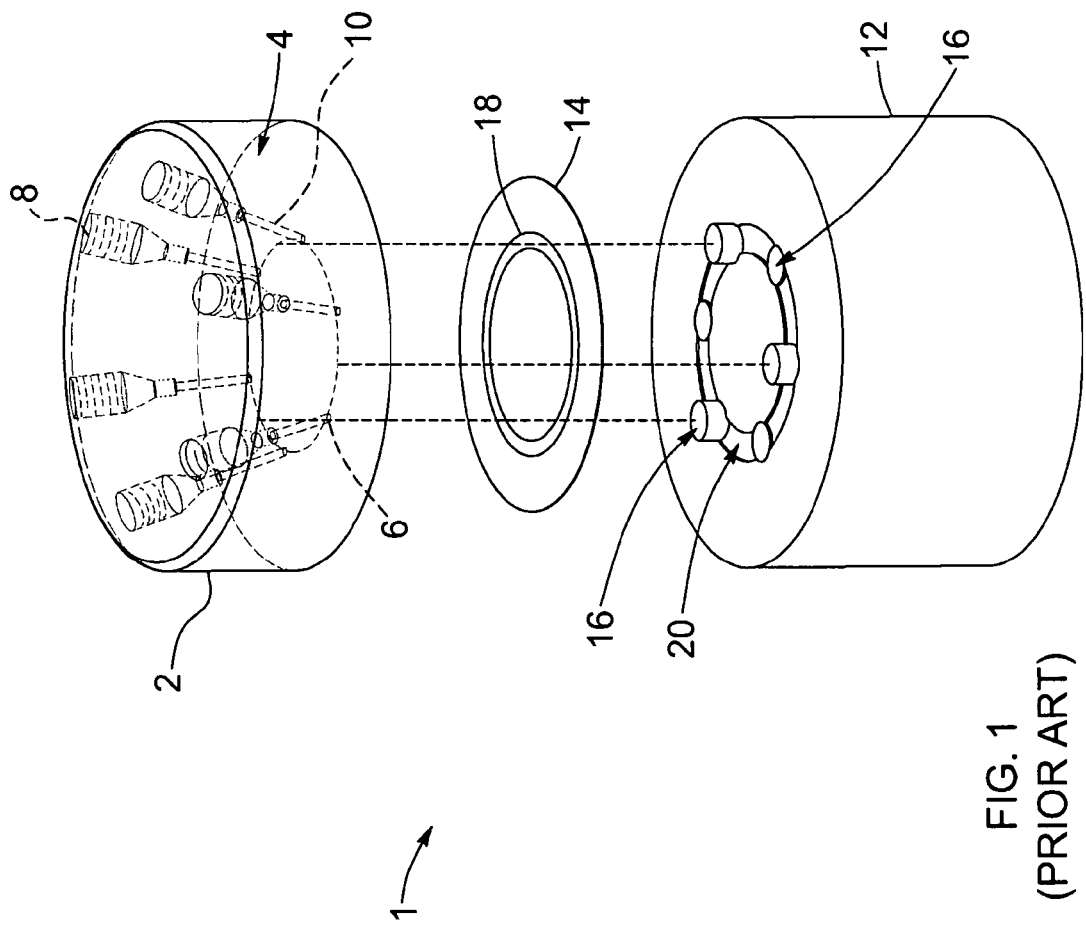
FIG. 1 (PRIOR ART) is an exploded perspective view of a diaphragm-sealed valve known in the art, in partial transparency.
Figure 2:
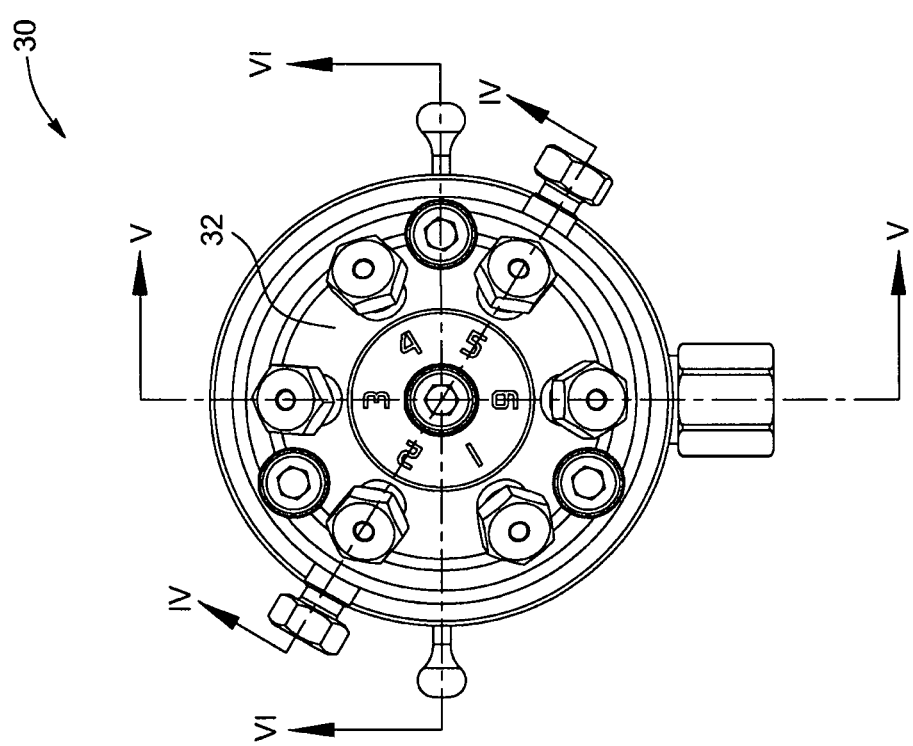
FIG. 2 is a top view of a diaphragm-sealed valve according to an embodiment.

In the following description, the same numerical references refer to similar elements. The embodiments, geometrical configurations, materials mentioned and/or dimensions shown in the figures or described in the present description are preferred embodiments only, given solely for exemplification purposes.

Moreover, although the embodiments of the valve and valve assembly and corresponding parts thereof consist of certain geometrical configurations as explained and illustrated herein, not all of these components and geometries are essential and thus should not be taken in their restrictive sense. It is to be understood, as also apparent to a person skilled in the art, that other suitable components and cooperation thereinbetween, as well as other suitable geometrical configurations, may be used for the valve and valve assembly, as will be briefly explained herein and as can be easily inferred herefrom by a person skilled in the art. Moreover, it will be appreciated that positional descriptions such as "above", "below", "left", "right" and the like should, unless otherwise indicated, be taken in the context of the figures and should not be considered limiting.

Referring generally to FIGS. 2 to 5 there is shown a valve 30 of the diaphragm-sealed type, according to an embodiment. Such a valve may be used in analytical equipments of various types, and more particularly in chromatographic equipment or online analyzers.

As illustrated in FIGS. 2 to 5, the valve 30 includes five main elements: a valve cap 32, a valve body 33, a diaphragm 36 compressibly positioned between the valve cap 32 and the valve body 33, a plurality of plungers 82 and an actuation system 220. The valve 30 may include a cylinder 34 and a bottom cap 40 or other equivalent structures forming the valve body 33 and allowing the plurality of plungers 82 and the actuating mechanism 96 of the actuation system 220 to be mounted to the valve body 33.

Valve Cap

Figure 3:
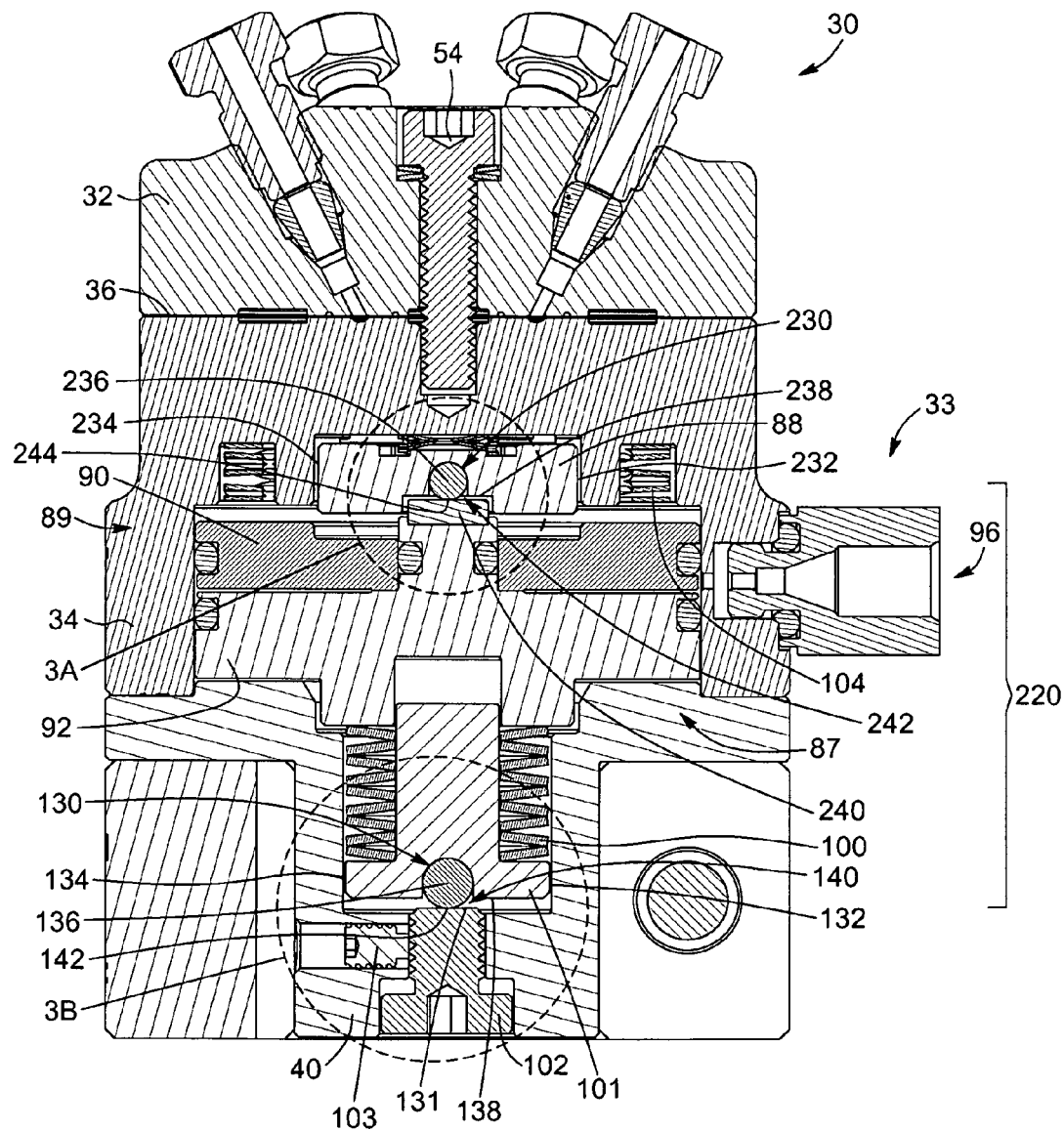
FIG. 3 is a cross-sectional side view of the diaphragm-sealed valve of FIG. 2 taken along line V-V.
Figure 4:
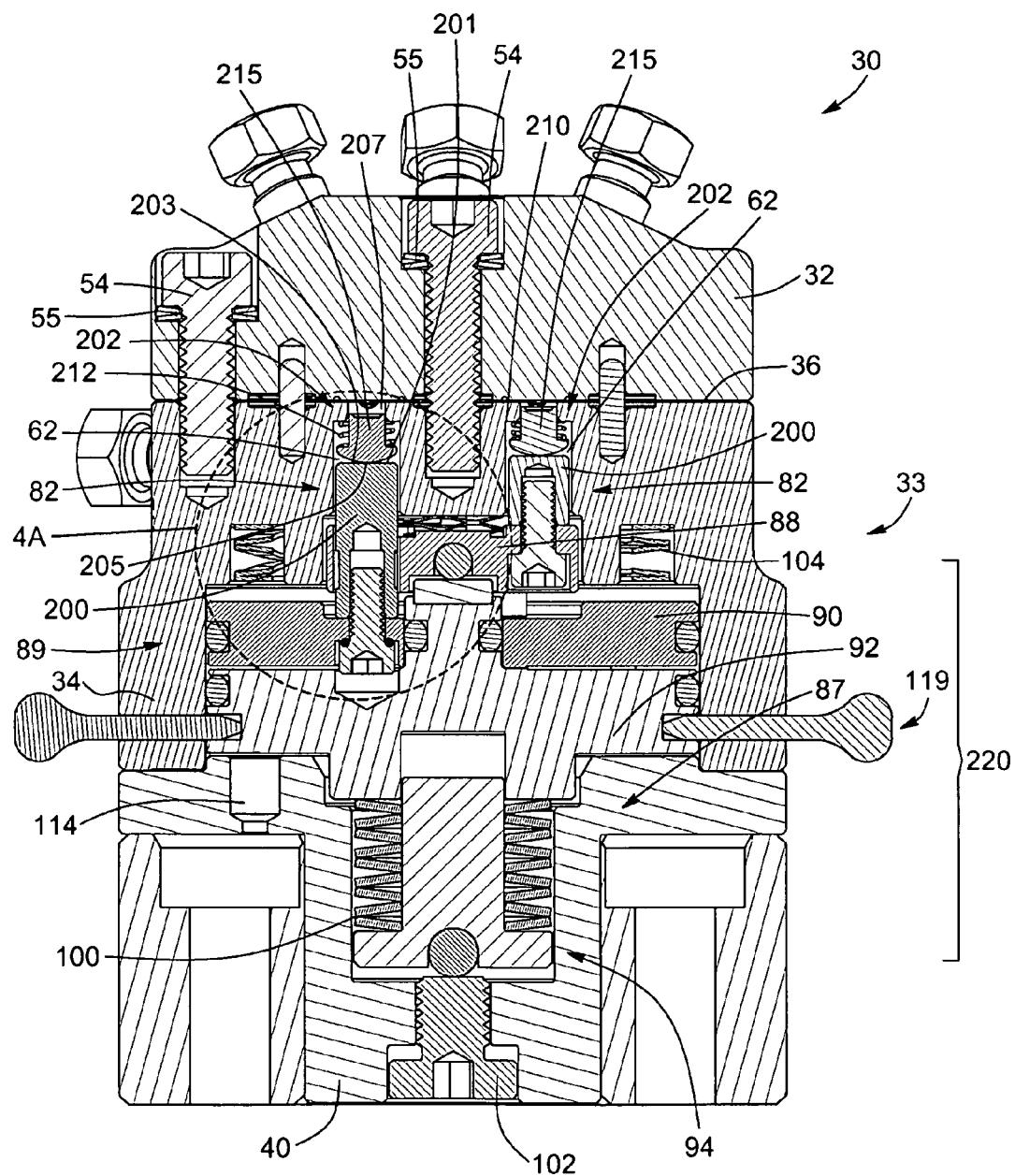
FIG. 4 is a cross-sectional side view of the diaphragm-sealed valve of FIG. 2 taken along line VI-VI.
Figure 5:
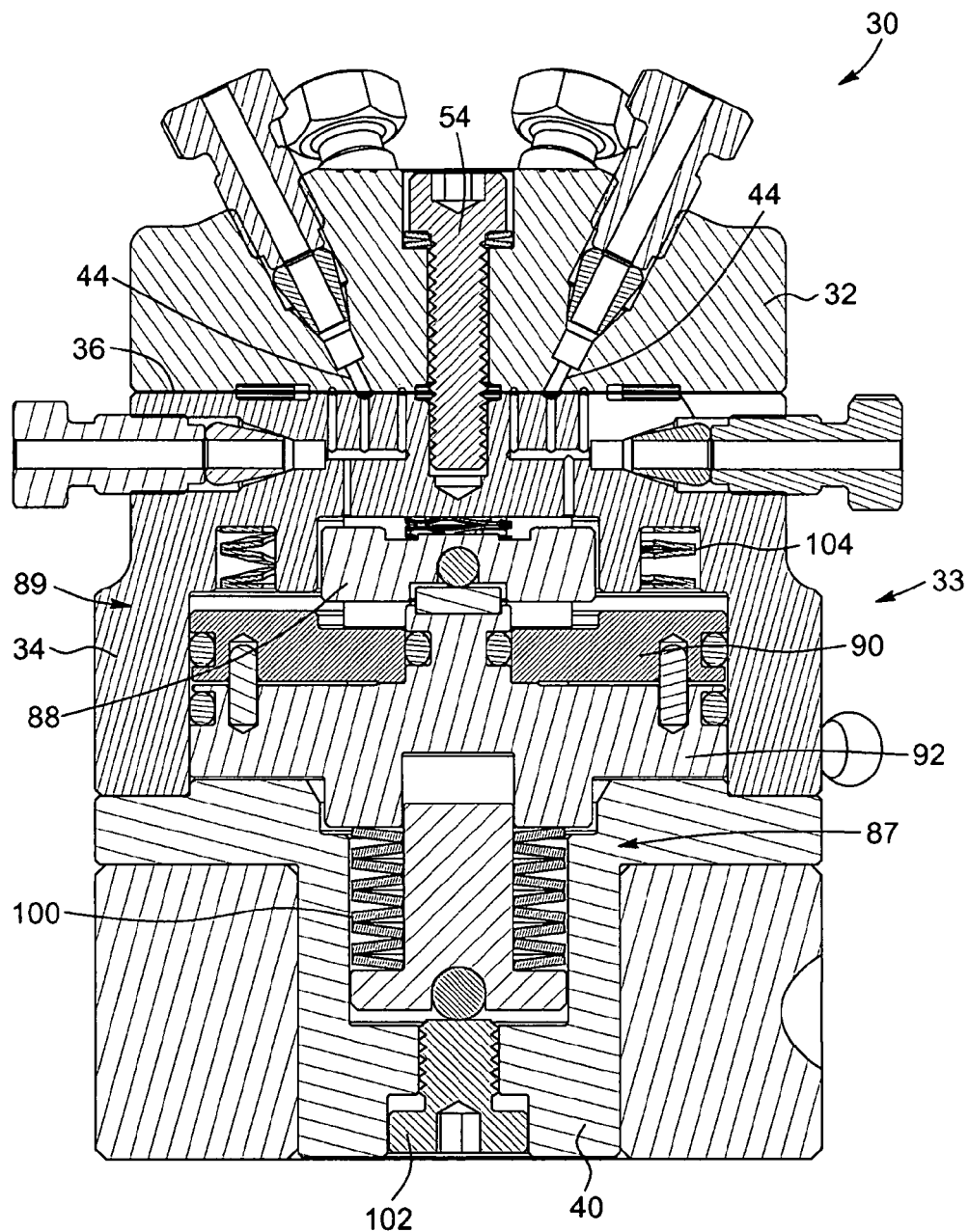
FIG. 5 is a cross-sectional side view of the diaphragm-sealed valve of FIG. 2 taken along line IV-IV.

Still referring to FIGS. 2 to 5 and additionally to FIGS. 6A to 6E, there is shown a valve cap 32 according to an embodiment. In the illustrated embodiment, the valve cap 32 has a plurality of process conduits 44 extending through it and an interface, hereinafter referred to as the valve cap interface 42. This valve cap interface 42 is flat and smooth, and is in contact with the diaphragm 36 when the valve is assembled (as shown in FIGS. 3 to 5). Each process conduit 44 ends in a process port 46 opening at the valve cap interface 42. In an embodiment, the process ports 46 are circularly arranged on the valve cap interface 42.

Best shown in FIG. 6C, in an embodiment, each one of the process conduits 44 is formed by a larger threaded hole 48 for receiving tubing connections and a smaller fluid passage 50 ending in the process port 46.

In the illustrated embodiment, the valve cap 32 has a cylindrical shape and is, for example and without being limitative, made of electro-polished stainless steel. The valve cap 32 is also provided with screw holes 52 for receiving socket head cap screws 54, for mounting the valve cap 32 to the cylinder 34. As can be seen on FIG. 4, in an embodiment, a biasing mechanism 55 such as, without being limitative, a Belleville washer stack, is provided between the head of the socket head cap screws 54 and the screw holes 52, in order to maintain a constant pressure on the diaphragm 36, between the valve cap 32 and valve body 33, independently of the temperature variation to which the valve may be subject to. Of course, other arrangements for holding the valve cap 32 to the cylinder 34 can be considered. Optionally, a layer of polymer may cover the valve cap interface 42 of the valve cap 32. Other materials, for example and without being limitative, ceramic or various types of polymers, may be used as material for the valve cap 32 or a portion thereof. One skilled in the art will readily understand that the valve cap 32 may present a different shape, form or configuration than the cylindrical one shown in the embodiment illustrated in the Figures. Of course, other embodiments of the valve cap may include 4, 8, 10, 12 or any other convenient number of process ports 46.

Cylinder

Now referring to FIGS. 3 to 5 and 7A to 7D, there is shown, for illustrative purposes, one embodiment of the cylinder 34 of the body 33 of the valve 30. Similarly to the valve cap 32 described above, the cylinder 34 also has an interface, hereinafter referred to as the valve body interface 58, which faces the valve cap interface 42 of the valve cap when the valve is assembled (as shown in FIGS. 3 to 5). Once again the valve body interface 58 is smooth and flat. The valve body interface 58 is provided with a main recess 60 having an outline matching the arrangement of the process ports 46 on the valve cap interface 42. Therefore in the illustrated embodiment where the process ports 46 are circularly arranged on the valve cap interface 42, the main recess 60 presents a circular outline. The main recess 60 is aligned with the process ports 46 of the valve cap 32 when the valve elements are assembled and the valve is ready for use (as in FIGS. 3 to 5).

The cylinder 34 also includes a plurality of plunger passages 62 each extending in the cylinder 34 and opening at one end in the main recess 60 between two of the process ports 46. The other ends of the plunger passages 62 open in a valve body cavity 63.

Figure 7B:
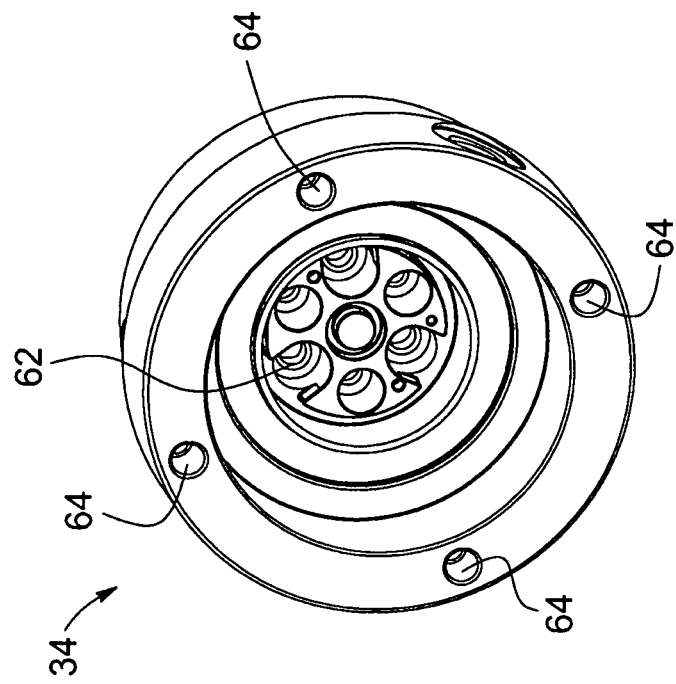
FIG. 7B is a bottom perspective view of the cylinder of FIG. 7A.
Figure 7A:
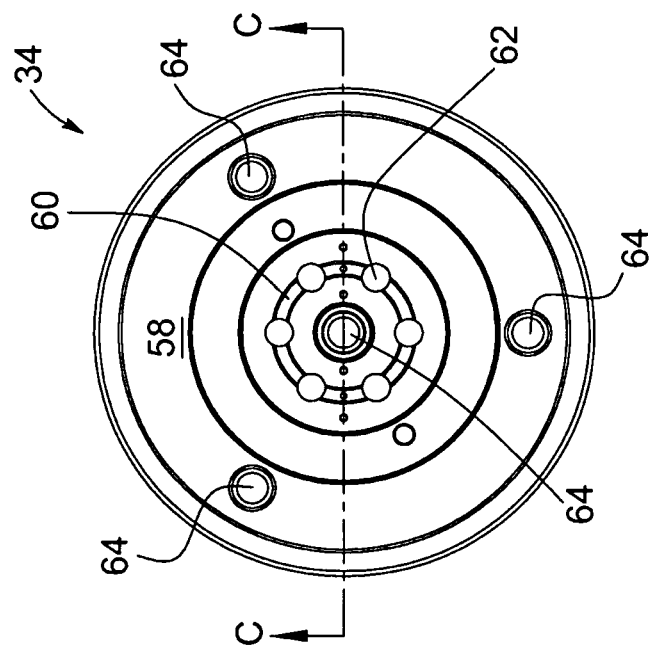
FIG. 7A is a top view of a cylinder of the valve body according to an embodiment.

The cylinder 34 is also provided with a first set of screw holes 64 for receiving the socket head cap screws 54 that hold the cylinder 34 to the valve cap (best shown in FIG. 7A) and a second set of screw holes 64 for receiving the socket head cap screws that hold the cylinder 34 to the bottom cap 40 (best shown in FIG. 7B). Of course, other arrangements could be considered for affixing the cylinder 34 to the valve cap 32 or the bottom cap 40.

Diaphragm

Now referring to FIGS. 8A to 8D, there is shown an embodiment of the diaphragm 36 of the valve 30. The diaphragm 36 has a first surface 74 facing the valve cap 32 and a second surface 76 facing the cylinder 34. The diaphragm 36 is compressibly positioned between the valve cap interface 42 and the valve body interface 58 when the valve is assembled and ready for use (as in FIGS. 3 to 5), such that the diaphragm is positioned across the process ports 46. As more clearly shown in FIG. 8C, the diaphragm preferably has a pre-formed deformation 78 which lays within the main recess 60 of the cylinder 34 when the valve is assembled. The first surface 74 of the diaphragm 36 and the valve cap interface 42 of the valve cap 32 define a communication channel between the process ports 46.

The diaphragm 36 can be made of a single layer of polymer or of multiple layers of polymer, with or without a thin metallic layer, or alternatively be made of metal only. For example, and without being limitative, metals that may be used are stainless steel 316, aluminum, chrome-nickel alloy, copper and the like. For applications requiring high gas-tightness sealing, a diaphragm 36 made of multiple layers of polymer is preferably used, while other applications require a thin metallic layer over the polymer layers.

Leaks Collection

With additional reference to FIGS. 7C and 7D, the cylinder 34 may also be provided with a leak collection system comprising a process purging channel 65 extending along the main recess 60, a process purging inlet passage 66 and process purging outlet passage 68. The process purging inlet passage 66 is connected to an entry 67 of a purge line, and the process purging outlet passage 68 is connected to an exit 69 of a purge line. The cylinder 34 may be further provided with a pair of fluid inlets 70 and a pair of fluid outlets 72, the pair of fluid inlets 70 also being connected to the entry 67 of a purge line, and the pair of fluid outlets 72 being connected to the exit 69 of the purge line.

The cylinder 34 may also be provided with actuation purging/venting outlet passages 112 allowing a flow of fluid towards the actuation system 220. The difference in diameter between the purging/venting outlet passages 112 dictates the direction of the flow, the fluid moving from the purging/venting outlet passage 112 having a smaller diameter to the one having a larger diameter.

As seen in FIG. 6D, a purge circulation line may further include inner and outer annular channels 51 and 53 extending at the valve cap interface 42 of the valve cap 32. In the illustrated embodiment, the fluid inlets 70 and the fluid outlets 72 each have a first opening in the inner annular channel 51 and a second opening in the outer annular channel 53.

The operation of such a leak collection system is described in detail in the present Applicant's above-mentioned application PCT/CA2008/002138, which is incorporated herein by reference, and will not be described further herein.

Plungers

Figure 4A:
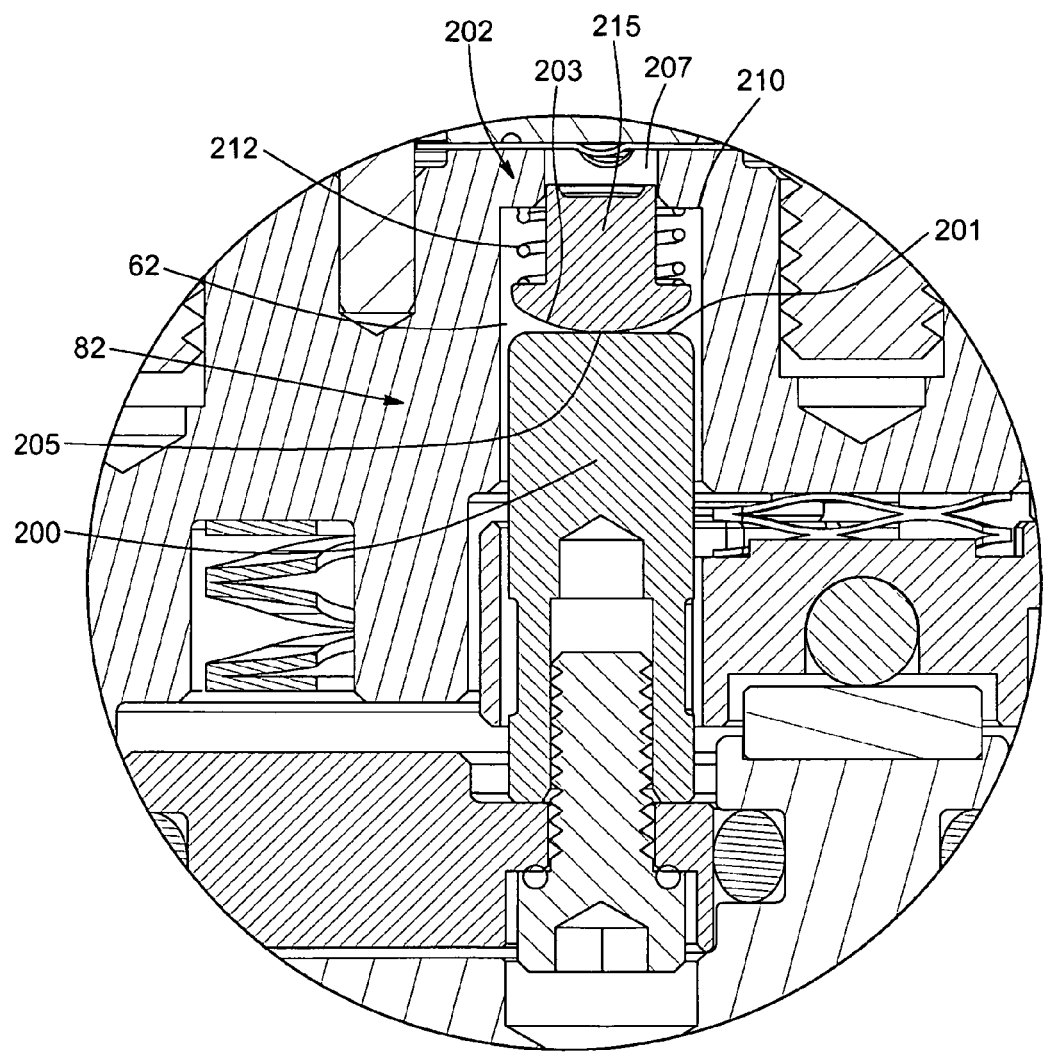
FIG. 4A is an enlarged view of section 4A of FIG. 4.
Figure 4B:
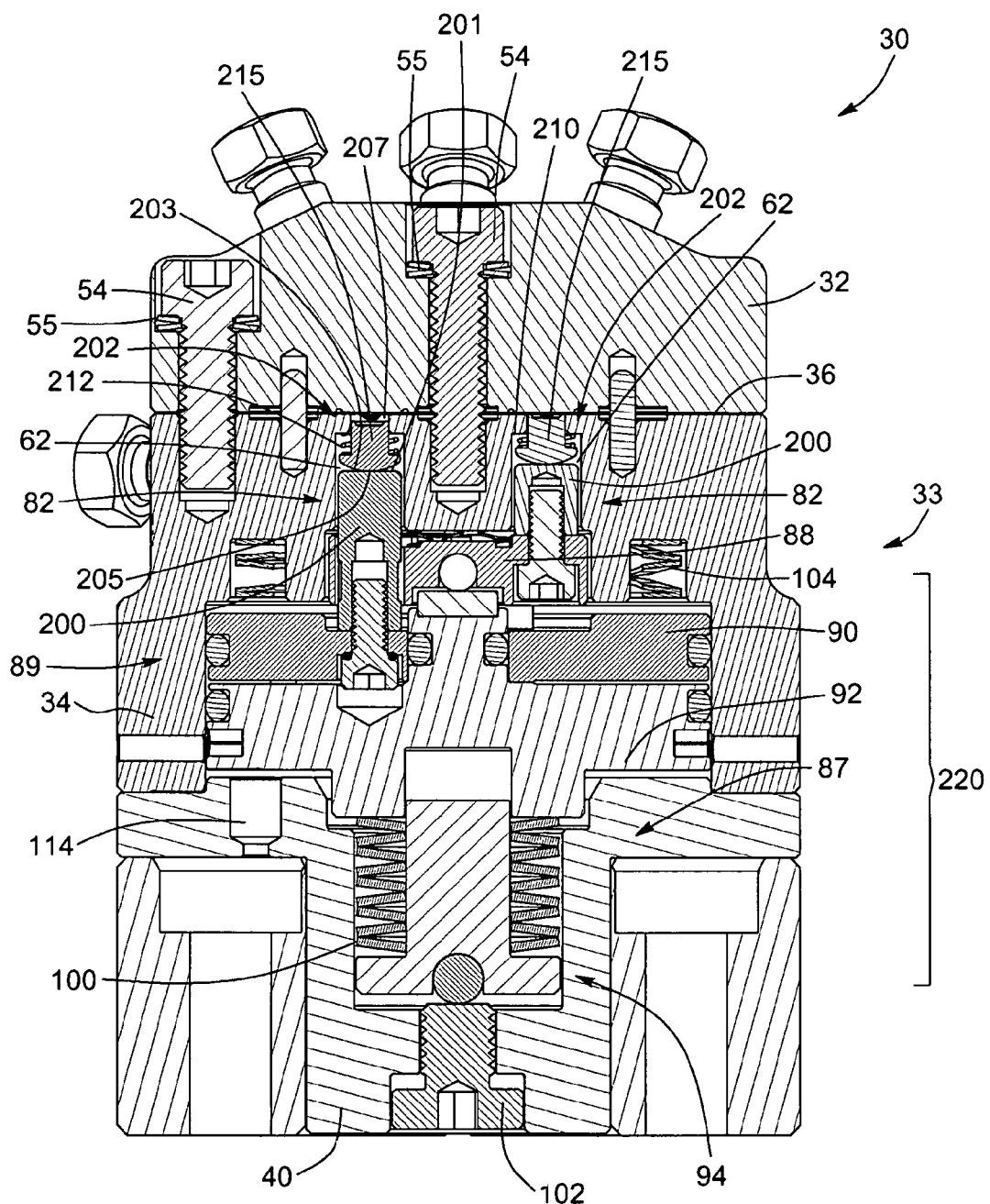
FIG. 4B is also a cross-sectional side view of the diaphragm-sealed valve of FIG. 2 taken along line VI-VI, where the locking pins are removed.

Now Referring to FIGS. 4, 4A and 4B, the valve 30 is further provided with a plurality of plungers 82 for engaging and disengaging the diaphragm 36, in order to allow or prevent communication between adjacent ports. The plungers 82 are each positioned in one of the plunger passages 62 of the cylinder 34. In the context of the present document, the term "plunger" is understood to mean a mechanical component or assembly driven by or against a mechanical force or fluid pressure.

In an embodiment, each plunger 82 is formed of a base section 200 and a top section 202. The base section 200 preferably has a cylindrical shape ending in a head 201 which projects upward in the passage. The top section 202 preferably includes a diaphragm-engaging portion 215 and a foot 203. In the illustrated embodiment the base section 200 and top section 202 are not physically attached, but meet at an interface 205 which represents a tangential contact point between the head 201 of the base section 200 and the foot 203 of the top section 202. In the present document, the term tangential contact point is understood to mean a point of contact at the tangent of two surfaces which come into contact. In the case of a rounded and a flat surface, the tangential contact point is at the tangent of the rounded surface where the flat surface comes into contact with the same. In the case of two rounded surfaces, the tangential contact point is at the common tangent where the two rounded surfaces come in contact.

One skilled in the art will understand that, in an alternative embodiment, the head 201 of the base section 200 and the foot 203 of the top section 202 could meet at an interface where the head 201 of the base section 200 and the foot 203 of the top section 202 present a flat configuration. Therefore, in this alternative embodiment, the contact between them would not be a tangential contact.

As can be seen in FIG. 4, in the illustrated embodiment, the top section 202 is located above the base section 200 of the plunger, within the corresponding plunger passage 62 of the cylinder 34. The head 201 of the base section 200 presents a flat configuration while the foot 203 of the top section 202 presents a rounded configuration. Therefore, contact between the head 201 and the foot 203 occurs at the tangent of the flat head 201 of the base section 200 and the rounded foot 203 of the top section 202. One skilled in the art will understand that in alternative embodiments, the head 201 of the base section could present a rounded configuration while the foot 203 of the top section would present a flat configuration, or they could both present a rounded configuration, while still providing a tangential contact point between them. Similarly, a configuration using a bearing, such as the one described below in reference to the Belleville washer support and the bottom cap screw or the piston and the push plate, between the head 201 of the base section 200 and the foot 203 of the top section 202, could also be used to provide the tangential contact point between these components.

In the alternative embodiment where the contact between the head 201 of the base section 200 and the foot 203 of the top section 202 is not a tangential contact, the head 201 of the base section 200 and the foot 203 of the top section 202 could both present an entirely flat configuration or either one of the head 201 of the base section 200 or the foot 203 of the top section 202 could present a combination of a rounded section and a flat section. In this embodiment, the head 201 of the base section 200 and the foot 203 of the top section 202 would come into contact at a point where both the head 201 of the base section 200 and the foot 203 of the top section 202 are flat.

Still referring to FIGS. 4, 4A and 4B, in the illustrated embodiment, each plunger passage 62 of the cylinder 34 of the valve body 33 comprises a shoulder 210. The plunger passage 62 therefore has a narrower portion 207 between the shoulder 210 and the valve body interface 58 of the cylinder 34. In order to adapt to such shoulder 210, the top section 202 of each plunger 82 is sized and shaped such that the diaphragm-engaging portion 215, which is located opposite to the foot 203 of the top section 202, is movable within the narrower portion 207 defined by the shoulder 210. The diaphragm-engaging portion 215 is therefore itself narrower than the foot 203 of the corresponding top section 202, which results in the foot 203 of the corresponding top section 202 being movable in the plunger passage 62, but being too large to enter the narrower portion 207.

A biasing mechanism 212 is provided between the shoulder 210 and the foot 203 of the top section 202, for biasing the top section 202 of each plunger 82 away from the diaphragm 36, when no pressure is exerted on the top section 202 by the base section 200. For example and without being limitative, the biasing mechanism can be a spring 212 surrounding a section of the diaphragm-engaging portion 215. The spring therefore abuts on the top surface of the foot 203 and the bottom surface of the shoulder 210, biasing the top section 202 downwards.

One skilled in the art will understand that the above described plunger configuration could work properly without the shoulder 210, as long as a biasing mechanism is provided to bias the top section 202 of each plunger 82 away from the diaphragm 36 when not pressured by the corresponding base section 200.

When the valve is activated, the plungers 82 can slide in the corresponding passage 62, between a closed position and an open position. For example, in FIG. 4B the right side plunger is shown in the closed position, whereas the left side plunger is shown in the open position.

In the closed position, the plunger 82 engages the diaphragm 36 between two adjacent ports, and therefore interrupts the communication between these ports. Engagement of the diaphragm 36 is effected by the base section 200 of a plunger 82 being moved upward and pressing against the top section 202. The pressure exerted by the base section 200 counteracts the biasing mechanism, for example by compressing the spring 212, the top section 202 is brought upward, and the diaphragm-engaging portion 215 engages the diaphragm 36.

In the open position, the plunger 82 is disengaged from the diaphragm 36 and therefore allows the communication between the two adjacent ports. The open position is reached when the base section 200 slides downward and away from the top section 202. When none or insufficient pressure is exerted on the top section 202 by the bottom section 200, the biasing mechanism acts to bias the top section 202 away from the diaphragm 36 in order to allow communication between the two adjacent ports.

In the illustrated embodiment both the bottom section 200 and top section 202 of the plungers 82 are cylindrical. However one skilled in the art will understand that the bottom section 200 and top section 202 may take other shapes than that of a cylinder, as long as they can result in the above-described open and closed position where communication between adjacent ports 46 is allowed in the open position and communication between adjacent ports 46 is prevented in the closed position.

The separation between the head 201 of the base section 200 and the foot 203 of the top section 202 of each plunger 82 results in the diaphragm engaging section 215 of the top section 202 of the plunger 82 contacting the diaphragm 36 perpendicularly even when the base section 200 of the plunger 82 is not perfectly perpendicular with the valve body interface 58 of the cylinder 34 or if the base sections 200 of the plungers 82 are not perfectly aligned with the top sections 202 of the plungers 82. Furthermore, if for any reason, the support structures (which will be described below) are not perfectly parallel with the valve body interface 58 of the cylinder 34, or if the alignment of the valve cap 32 with the cylinder 34 is not perfectly tuned, the top sections 202 of the plungers 82 will remain perpendicular with the valve body interface 58 of the cylinder 34 when a support structure is forced up by the action of the actuating gas, as will be described below.

Actuation System

In order for the plungers 82 to be movable between the open and closed position, the base section 200 of each plunger 82 is connected to an actuation system 220. The base section 200 is connected to the actuation system 220 such that the head 201 of each base section 200 projects away therefrom. For example and without being limitative, a screw can be used to mount the base section 200 of the plunger 82 to the actuation system 220.

As better seen in FIG. 3, in an embodiment, the actuation system 220 includes a first support structure 87 comprising a push plate 88 and a first piston 92 as well as a second support structure 89 comprising a second piston 90. As illustrated, the first piston 92 is located below the second piston 90 and for simplicity these two pistons will hereinafter be referred to as the lower piston 92 and the upper piston 90, respectively.

In the illustrated embodiment, each plunger 82 is either normally closed or normally opened. The base sections 200 of the normally closed plungers are mounted on the push plate 88 and the base sections 200 of the normally open plungers are mounted on the second piston 90.

The push plate 88 extends within the cavity 63 of the cylinder 34, in parallel to the valve body interface 58 of the cylinder 34, i.e. perpendicular to the plunger passages 62 and a central axis of the cylinder 34. The push plate 88 is movable transversally to the valve body interface 58, or in other words in parallel to the central axis of the cylinder 34. The bottom sections 200 of the normally closed plungers 82 are mounted on the push plate 88. A plurality of cavities extend across the push plate 88 for allowing the bottom sections 200 of the normally open plungers 82 to move therethrough. The upper piston 90 extends contiguously under the push plate, the bottom sections 200 of the normally open plungers 82 being mounted on it. The lower piston 92 extends under the upper piston 90 contiguously to it.

Figure 3A:
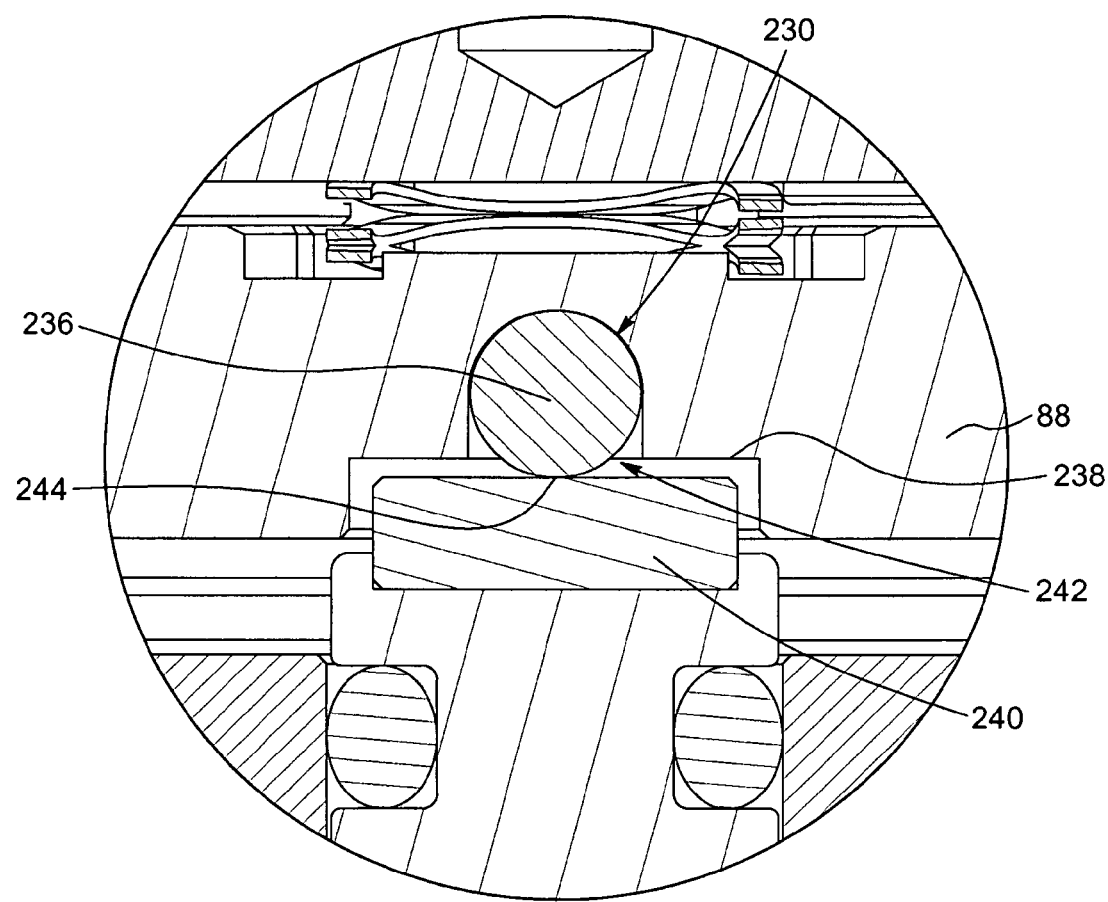
FIG. 3A is an enlarged view of section 3A of FIG. 3.

As can be seen in FIGS. 3 and 3A, the push plate 88 is provided with a bearing receiving section 230 centered between its right side extremity 232 and left side extremity 234. The bearing receiving section 230 is located in a bottom wall 238 of the push plate 88, thereby forming a downward extending cavity. The cavity formed by the bearing receiving section 230 is sized and shaped for receiving therein a first portion of a bearing 236. It should be understood that in the present document, the term "bearing" is used to refer to any spherical body or ball made of hardened material and having a smooth surface in order to provide rolling abutment between adjacent surfaces. A second portion of the bearing 236 projects downwardly away from the bottom wall 238. This second portion is referred to as the projecting portion 242. The size of the bearing 236 may be such that the first portion closely matches the inside of the bearing receiving section 230, thereby preventing any looseness between the two components, while allowing the bearing 236 to roll freely therein. The lower piston 92 engages the push plate 88 at a single tangential contact point 244 between the bearing 236 and a top section 240 of the lower piston 92. The tangential contact point 244 is provided by the rounded configuration of the bearing 236 and the flat configuration of the top section 240 of the lower piston 92, and allows a rolling abutment between the lower piston 92 and the push plate 88. Such a configuration prevents a misalignment of the push plate 88 within the cavity 63 of the cylinder 34, which would result in a misalignment of the plungers 82, by allowing the push plate 88 to automatically be re-centered when the plungers 82 are pushed against the diaphragm 36.

In the illustrated embodiment, the top section 240 of the lower piston 92 is a separate part made of a hardened material such as, without being limitative stainless steel 17-4 PH, in order to provide a high hardness material at the contact point. However, in an embodiment the top section 240 could also be integral with the lower piston 92.

O-rings are preferably provided on the outline of each piston, to properly seal the upper 92 and lower 90 pistons to the inner surface of the cylinder 34. In the illustrated embodiment, when either the upper piston 90 or the lower piston 92 are retracted, the corresponding bottom sections 200 of the plungers 82 attached thereto are pulled downward, resulting in a release of the pressure exerted on the top sections 202.

As can be seen in FIG. 3, biasing mechanisms 94 are provided such that the lower piston 92 is upwardly biased and that the upper piston 90 is downwardly biased. In an embodiment, a Belleville washer support 101 and a Belleville washer assembly 100 cooperate to bias the lower piston 92 upwardly. A bottom cap load screw 102 may be provided to control an upward force on the Belleville washer support 101. Still according to an embodiment, a wave spring 104 extending over the upper piston 90 exerts a downward force on the upper piston 90 and therefore downwardly biases the upper piston 90. One skilled in the art will understand that, in alternative embodiments, different biasing assembly may be provided for biasing the lower piston 92 upwardly and the upper piston 90 downwardly.

To actuate the plungers, an actuating mechanism 96 is provided to control a distance or space between the upper piston 90 and the lower piston 92. In this embodiment, it can be seen that the actuating mechanism 96 actuates the plungers 82 between the open and closed positions, for example by injection of an actuation gas between the upper piston 90 and the lower piston 92, the actuating mechanism 96 being pneumatic actuators.

Figure 3B:
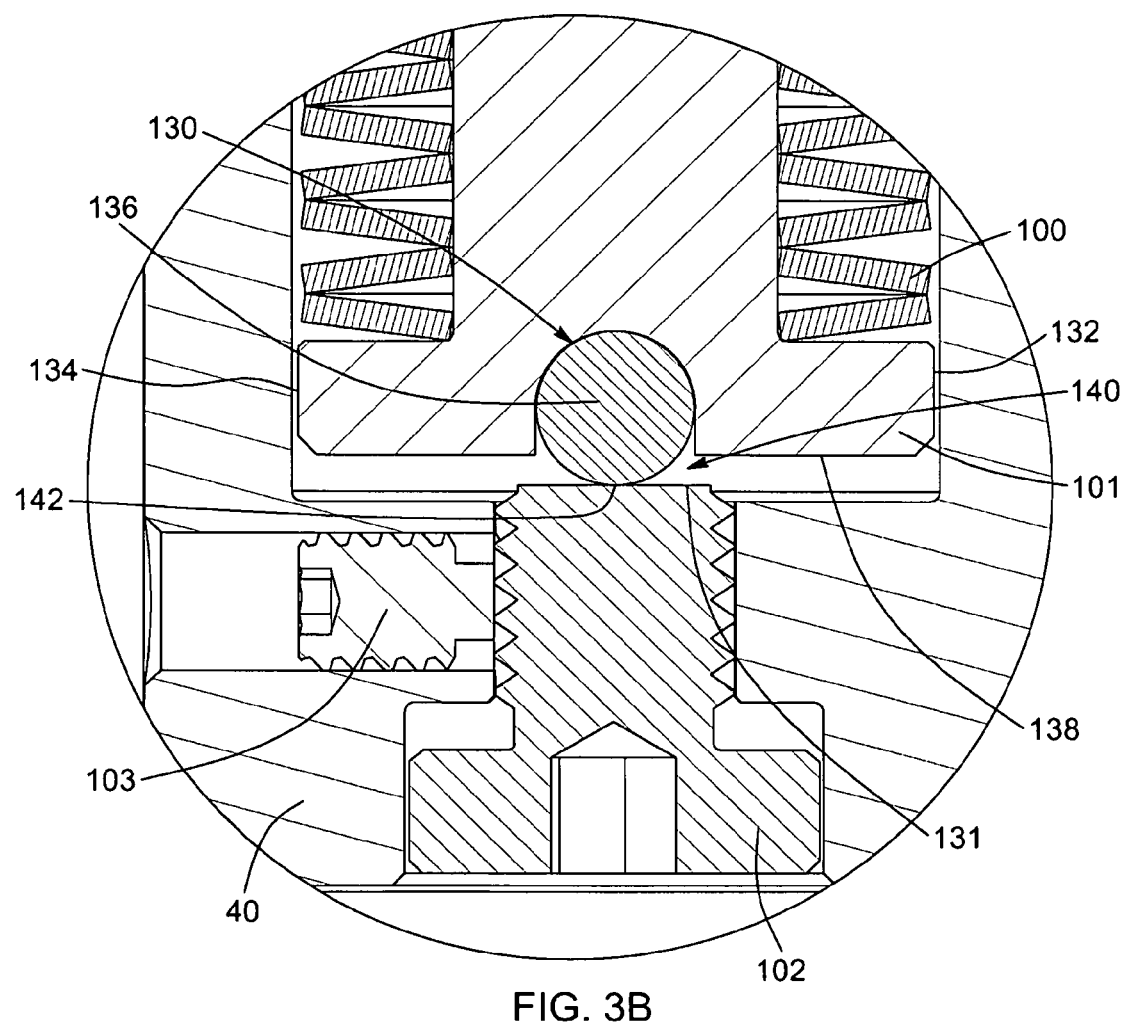
FIG. 3B is an enlarged view of section 3B of FIG. 3.

As can be seen in FIGS. 3 and 3B, the bottom cap 40 is affixed to the cylinder 34, preferably with socket head cap screws, and it also houses the bottom cap load screw 102 that allows adjustment of the pressure exerted on the lower piston 92 via the Belleville washer support 101 and Belleville washer assembly 100. To facilitate the alignment of the actuation system 220 subsequent to the pressure exerted by the bottom cap load screw 102 on the Belleville washer support 101, the Belleville washer support 101 may be provided with a bearing receiving section 130 centered horizontally between its right side extremity 132 and left side extremity 134. The bearing receiving section 130 is located on a bottom wall 138 of the Belleville washer support 101 and forms a downward extending cavity. The cavity formed by the bearing receiving section 130 is sized and shaped for receiving therein a first portion of a bearing 136. A second portion of the bearing 136 projects downwardly away from the bottom wall 138 of the Belleville washer support 101. This second portion is referred to as the projecting portion 140. The size of the bearing 136 is such that it closely matches the inside of the bearing receiving section 130, thereby preventing any looseness between the bearing 136 and the bearing receiving section 130, while allowing the bearing 136 to roll freely therein. The bottom cap load screw 102 engages the Belleville washer support 101 at a single tangential contact point 142 between the bearing 136 and a top section 131 of the bottom cap load screw 102. The tangential contact 142 is provided by the rounded configuration of the bearing 136 and the flat configuration of the top section 131 of the bottom cap load screw 102. The single tangential contact point 142 prevents a misalignment of the actuation system resulting from the bottom cap load screw 102 exerting an off-centered pressure on the Belleville washer support 101, which in turn would cause a misalignment of the lower piston 92. Such an off-centered pressure of the bottom cap load screw 102 on the Belleville washer support 101 can be encountered in prior art valves, since the locking screw 103 used for locking the bottom cap load screw 102 in place tends to shift the position of the bottom cap load screw 102 from its centered position.

In an embodiment, the bottom cap 40 can also be provided with a bottom cap actuation vent 114 extending in it and located opposite to the actuating mechanism 96, for preventing pressure build up between the lower piston 92 and the bottom cap 40.

The operation of such an actuation vent 114 is described in detail in the present Applicant's above-mentioned application PCT/CA2009/001783 which is incorporated herein by reference, and will not, as such, be described further herein.

One skilled in the art will easily understand that even though a preferred actuation system is described herein, in alternative embodiments, any other actuation system resulting in the movement of the plungers between a closed and an open position could be used.

Locking Mechanism

Oftentimes, after diaphragm valves are built and fully tested, they are sealed in plastic packages, packed and stored in inventory before shipping to customers. Depending on various factors such as market demand, inventory management, customer need and the like, valves are likely to stay unused for weeks or months after their manufacture. In addition, in some circumstances a valve owner may temporarily shut down or remove a valve from active use for an undetermined amount of time before putting it in service again. While a valve is idle (as shown in FIG. 4B), its normally closed plungers are in their closed position and therefore apply a constant pressure on the diaphragm. Depending on diaphragm material, this could lead to a permanent deformation of the diaphragm, and reduced efficiency of the valve. A locking mechanism is therefore advantageous to lock the normally closed base sections 200 of the plungers 82 in their open position (as shown in FIG. 4) when the valve is not in use.

In an embodiment, a locking mechanism 119 advantageously engages the first support structure 87 when the base sections 200 of the normally closed plungers 82 are in an open position, thereby acting against the biasing mechanisms 94 and physically preventing the plungers 82 from reaching a closed position where the top section 202 is pushed against the diaphragm 36. As will be appreciated by one of ordinary skill in the art, the use of such a locking mechanism 119 can advantageously be used to prevent closed plungers 82 from deforming, compressing or otherwise acting upon the diaphragm 36 when the valve 30 is not in use.

It will also be appreciated that such locking mechanism 119 can also advantageously ease replacement of the diaphragm during maintenance and the like. By enabling a user to restrain the normally closed base sections 200 of the plungers within the valve body, it can be assured that the plungers do not interfere with the proper positioning of the diaphragm.

Different possible embodiments of such a locking mechanism is described in detail in the present Applicant's above-mentioned application PCT/CA2009/001783 which is incorporated herein by reference, and will not, as such, be described further herein.

Several alternative embodiments and examples have been described and illustrated herein. The embodiments described above are intended to be exemplary only. A person skilled in the art would appreciate the features of the individual embodiments, and the possible combinations and variations of the components. A person skilled in the art would further appreciate that any of the embodiments could be provided in any combination with the other embodiments disclosed herein. It is understood that the invention may be embodied in other specific forms without departing from the central characteristics thereof. The present examples and embodiments, therefore, are to be considered in all respects as illustrative and not restrictive, and the invention is not to be limited to the details given herein. Accordingly, while specific embodiments have been illustrated and described, numerous modifications come to mind without significantly departing from the scope of the invention as defined in the appended claims.

The invention claimed is:

1. A valve comprising:
   a valve cap having a plurality of process conduits extending therethrough, each one of the plurality of process conduits ending in a process port at a valve cap interface;
   a valve body having a valve body interface facing the valve cap interface, the valve body having a plurality of plunger passages extending therein;
   a diaphragm positioned between the valve cap interface and the valve body interface, across the process ports;
   a plurality of plungers, each one of the plurality of plungers being positioned in a corresponding plunger passage of the plurality of plunger passages and being movable between a closed position where the plunger engages the diaphragm, and an open position where the plunger is disengaged from the diaphragm; and
   an actuation system for moving each one of the plurality of plungers between the closed position and the open position;
   wherein each one of the plurality of plungers comprises:
   (i) a base section connected to the actuation system and having a head projecting away therefrom;
   (ii) a top section extending between the base section and the diaphragm, the top section having a foot in contact with the head of the base section; and
   (iii) a plunger biasing mechanism biasing the top section away from the diaphragm when the plunger is in the open position.

2. A valve according to claim 1, wherein the foot of the top section is in tangential contact with the head of the base section.

3. A valve according to claim 2, wherein at least one of the head of the base section and the foot of the top section presents a rounded configuration and the other one the head of the base section and the foot of the top section includes one of a flat configuration and a rounded configuration.

4. A valve according to claim 3, wherein the head of the base section includes a flat configuration and the foot of the top section includes a rounded configuration.

5. A valve according to claim 1, wherein each one of the plurality of plunger passages of the valve body comprises a shoulder defining a narrower portion of said passage between the shoulder and the valve body interface, and wherein the top section of each one of the plurality of plungers is sized and shaped such that a diaphragm-engaging portion of the top section is narrower than the foot and is movable in the narrower portion of the passage.

6. A valve according to claim 5, wherein the plunger biasing mechanism of each one of the plurality of plungers is located between the shoulder of a corresponding one of the plurality of plunger passages and the foot of the top section of the plunger.

7. A valve according to claim 6, wherein the plunger biasing mechanism comprises a spring.

8. A valve according to claim 1, wherein the actuation system comprises a piston.

9. A valve according to claim 8, wherein the actuation system further comprises:
   a push plate having a horizontally centered bearing receiving section formed therein, at least one of the plurality of plungers being mounted on the push plate; and
   a bearing located within the bearing receiving section of the push plate and projecting therefrom, a projecting portion of the bearing being in tangential contact with the piston and being the single point of contact between the piston and the push plate.

10. A valve according to claim 8, wherein the actuation system further comprises:
    a piston biasing mechanism for biasing the piston of the actuation system upwardly, the piston biasing mechanism comprising:
    a support having a horizontally centered bearing receiving section formed therein;
    a piston biasing element positioned between a section of the support and the piston;
    a bottom cap screw for adjustably pressuring the support towards the piston; and
    a bearing located within the bearing receiving section of the support and projecting therefrom, a projecting portion of the bearing being in tangential contact with the bottom cap screw and being the single point of contact between the support and the bottom cap screw.

11. A valve according to claim 10, wherein the support comprises a Belleville washer support and the piston biasing element comprises a Belleville washer assembly.

12. The valve according to claim 1, wherein
the actuation system comprises:
- a first actuation component having a horizontally centered bearing receiving section formed therein;
- a first bearing located within the bearing receiving section of the first actuation component and projecting therefrom, a projecting portion of the first bearing being in tangential contact with a second actuation component of the actuation system and being the single point of contact between the first actuation component and the second actuation component;

a biasing mechanism for biasing the second actuation component of the actuation system upwardly, the biasing mechanism comprising:
- a first biasing component having a horizontally centered bearing receiving section formed therein;
- a biasing element positioned between a section of the first biasing component and the second actuation component; and
- a second bearing located within the bearing receiving section of the first biasing component and projecting therefrom, a projecting portion of the second bearing being in tangential contact with a second biasing component of the biasing system and being the single point of contact between the first biasing component and the second biasing component.

13. A valve according to claim 12, wherein the first actuation component comprises a push plate and the second actuation component comprises a piston, and wherein the first biasing component comprises a support and the second biasing component comprises a bottom cap screw.

14. A valve according to claim 13, wherein the support comprises a Belleville washer support and the biasing element comprises a Belleville washer assembly.

15. The valve according to claim 1, wherein
the actuation system comprises:
- a piston;
- a push plate having a horizontally centered bearing receiving section formed therein, at least one of the plurality of plungers being mounted on the push plate; and
- a bearing located within the bearing receiving section of the push plate and projecting therefrom, a projecting portion of the bearing being in tangential contact with the piston and being the single point of contact between the piston and the push plate.

16. The valve according to claim 15, comprising:
a biasing mechanism for biasing the piston of the actuation system upwardly, the biasing mechanism comprising:
- a support having a horizontally centered bearing receiving section formed therein;
- a piston biasing element positioned between a section of the support and the piston;
- a bottom cap screw for adjustably pressuring the support towards the piston; and
- a bearing located within the bearing receiving section of the support and projecting therefrom, a projecting portion of the bearing being in tangential contact with the bottom cap screw and being the single point of contact between the support and the bottom cap screw.

17. A valve according to claim 16, wherein the support comprises a Belleville washer support and the piston biasing element comprises a Belleville washer assembly.

18. A valve comprising:
a first interface and a second interface facing one another;
a plurality of process conduits, each one of the plurality of process conduits ending in a process port on the first interface;
a plurality of plunger passages opening on the second interface;
a diaphragm positioned between the first interface and the second interface, across the process ports;
a plurality of plungers, each one of the plurality of plungers being positioned in a corresponding plunger passage of the plurality of plunger passages and being movable between a closed position where the plunger engages the diaphragm, and an open position where the plunger is disengaged from the diaphragm; and
an actuation system for moving each one of the plurality of plungers between the closed position and the open position;
wherein each one of the plurality of plungers comprises:
(i) a base section connected to the actuation system and having a head projecting away therefrom;
(ii) a top section extending between the base section and the diaphragm, the top section having a foot in contact with the head of the base section; and
(iii) a plunger biasing mechanism biasing the top section away from the diaphragm when the plunger is in the open position.

* * * * *